US 9,000,767 B2

(12) United States Patent
Schmidt

(10) Patent No.: US 9,000,767 B2
(45) Date of Patent: Apr. 7, 2015

(54) MAGNETIC RESONANCE SYSTEM AND METHOD FOR CARRYING OUT MAGNETIC RESONANCE MEASUREMENTS IN AN INTRAORAL REGION

(75) Inventor: Sebastian Schmidt, Weisendorf (DE)

(73) Assignee: Siemens Aktiengesellschaft, München (DE)

(*) Notice: Subject to any disclaimer, the term of this patent is extended or adjusted under 35 U.S.C. 154(b) by 467 days.

(21) Appl. No.: 13/429,207

(22) Filed: Mar. 23, 2012

(65) Prior Publication Data

US 2013/0076354 A1 Mar. 28, 2013

(30) Foreign Application Priority Data

Mar. 25, 2011 (DE) .................... 10 2011 006 150

(51) Int. Cl.
*G01V 3/00* (2006.01)
*G01R 33/56* (2006.01)
*G01R 33/34* (2006.01)
*G01R 33/565* (2006.01)
*G01R 33/341* (2006.01)
*A61B 5/055* (2006.01)
*A61B 5/00* (2006.01)

(52) U.S. Cl.
CPC ...... *G01R 33/5608* (2013.01); *G01R 33/34084* (2013.01); *G01R 33/56563* (2013.01); *G01R 33/341* (2013.01); *A61B 5/055* (2013.01); *A61B 5/447* (2013.01); *G01R 33/34076* (2013.01)

(58) Field of Classification Search
CPC .................................. G01R 33/285

USPC ............ 324/318, 322, 321, 309, 306
See application file for complete search history.

(56) References Cited

U.S. PATENT DOCUMENTS

| | | | | |
|---|---|---|---|---|
| 6,402,707 | B1 * | 6/2002 | Ernst | 600/590 |
| 7,295,007 | B2 * | 11/2007 | Dold | 324/307 |
| 7,366,562 | B2 * | 4/2008 | Dukesherer et al. | 600/424 |
| 2005/0035763 | A1 | 2/2005 | Canda et al. | |
| 2008/0068012 | A1 | 3/2008 | Werthner | |

FOREIGN PATENT DOCUMENTS

| | | |
|---|---|---|
| DE | 103 37 241 A1 | 3/2005 |
| DE | 10 2006 033 248 A1 | 1/2008 |

OTHER PUBLICATIONS

German Office Action dated Sep. 26, 2011 for corresponding German Patent Application No. DE 10 2011 006 150.9 with English translation.

O. Tymofiyeva et al., "In Vivo MRI-Based Dental Impression Using an Intraoral RF Receiver Coil," Wiley Periodicals Inc., pp. 244-251, 2008.

Sirona The Dental Company, CEREC Bluecam, Sehen Sie Cerec in Einem Neuen Licht, Webpage, http://sirona.de/ecomaXL/index.php?site=SIRONA_cerec_neuheiten_2009_bluecam, 2008.

* cited by examiner

*Primary Examiner* — Louis Arana

(74) *Attorney, Agent, or Firm* — Lempia Summerfield Katz LLC

(57) ABSTRACT

The present embodiments relate to a magnetic resonance system for carrying out magnetic resonance measurements in an intraoral region. The magnetic resonance system includes a magnetic resonance coil element and an intraoral measuring device that measures the position of a number of measuring points situated in the intraoral region.

20 Claims, 2 Drawing Sheets

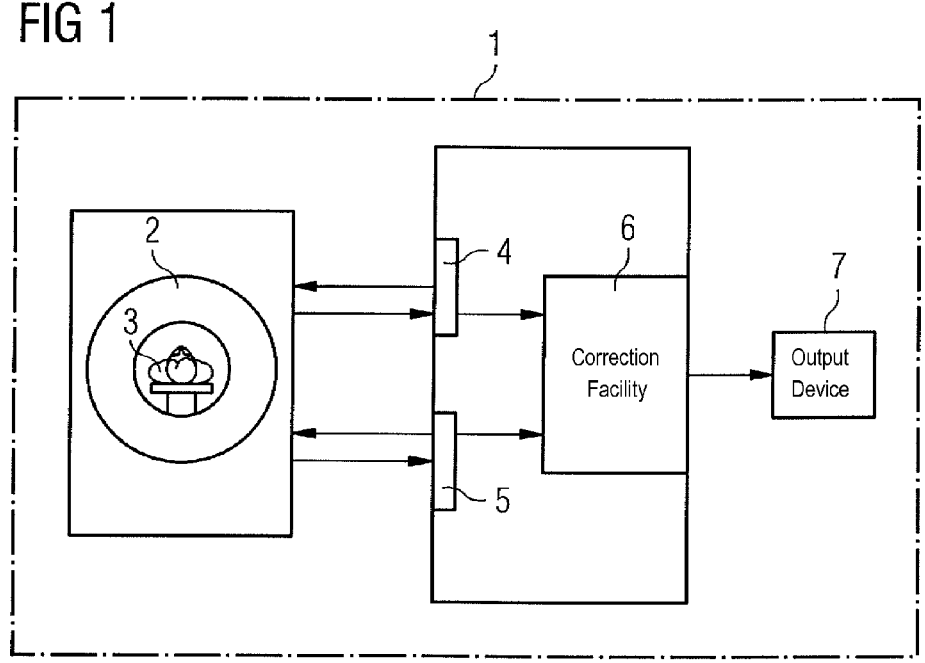
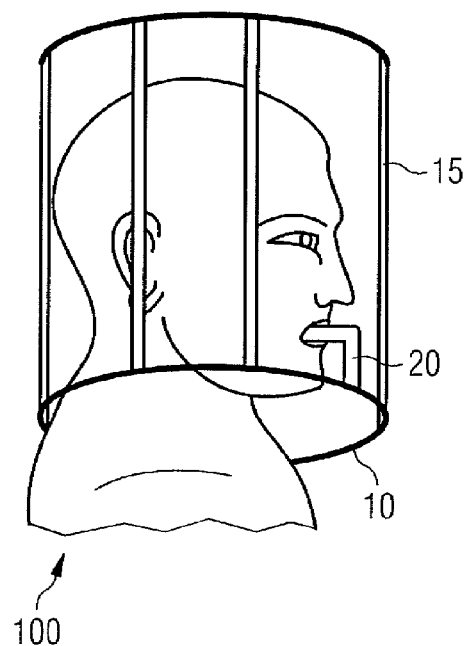

MAGNETIC RESONANCE SYSTEM AND METHOD FOR CARRYING OUT MAGNETIC RESONANCE MEASUREMENTS IN AN INTRAORAL REGION

This application claims the benefit of DE 10 2011 006 150.9, filed on Mar. 25, 2011.

BACKGROUND

The present embodiments relate to a magnetic resonance system and a method for carrying out magnetic resonance measurements in an intraoral region.

Diseases of the teeth and of the periodontium (e.g., periodontitis or caries) are diagnosed using X-ray based imaging methods. X-ray technologies employed for this purpose range from conventional X-ray methods, through digital X-ray methods in projection mode to new types of 3D X-ray methods.

In 3D diagnostic radiology, digital volume diagnostics (DVT) systems are on the market. Complete jaw regions may be radiographed or, additionally, high-resolution 3D images of tooth and jaw regions may be produced. The radiation used in digital systems is reduced in comparison with conventional diagnostics, and an image is immediately available. The DVT systems pet nit a type of X-ray computer tomography of the teeth and of the visceral cranium at a high resolution and positional accuracy. Such DVT diagnostic systems are, however, very complex and expensive, which provides that 3D diagnostic radiology is used only in a few indications. There is therefore a need for new imaging systems and methods in the jaw region.

For many diseases of the teeth or of the periodontium, a magnetic resonance tomography (MRT) examination is a good alternative to the previous methods such as, for example, diagnostic radiology, since MRT is free from ionizing radiation and also enables contrast in soft tissue to be better represented.

In a magnetic resonance device, the body to be examined may be subjected to a relatively high basic magnetic field of 3 or 7 tesla, for example, with the aid of a basic magnetic field system. In addition, a magnetic field gradient is created with the aid of a gradient system. Using a high-frequency send system, high-frequency magnetic resonance excitation signals (HF signals) are sent out by suitable antennas. This may result in the nuclear spins of certain atoms resonantly excited by this high-frequency field being tilted by a defined flip angle with respect to the magnetic field lines of the basic magnetic field. When the nuclear spins are relaxed, high-frequency signals (e.g., magnetic resonance signals) are emitted. The magnetic resonance signals are received by suitable receive antennas and processed further. From the "raw data" thus acquired, the desired magnetic resonance image data (MR image data) may be reconstructed. A position encoding is effected by switching appropriate magnetic field gradients in the different spatial directions at precisely specified times (e.g., when sending out the HF signals and/or when receiving the magnetic resonance signals). The high-frequency signals for the nuclear spin magnetization may be sent out by a "whole body coil" or "body coil" permanently incorporated in the magnetic resonance tomograph. A typical construction for this is a cage antenna (e.g., a birdcage antenna) that consists of a plurality of send rods that are arranged running parallel to the longitudinal axis around a patient chamber of the tomograph, in which an object under examination (e.g., a patient) is situated for the examination. On a face side the antenna, rods are each connected to one another in the form of a ring. In order to receive the magnetic resonance signals, local coils that are attached close to or directly on the body of the object under examination may be used. Such local coils include one or more conductor loops.

Non-bony tissue structures may be represented in position-related and tissue-specific fashion by MRT. Areas of application for MRT in the jaw region existing hitherto lie principally in the examination of the temporomandibular joints or of the floor of the mouth. Intraoral local coils for a dental MRT that enable an anatomical representation of the jaw region and also the representation of dental diseases are thus known.

MRT diagnostics have, however, hitherto not yet become established in tooth imaging or imaging in the jaw region because only very inexpensive MR systems are suitable in this area for economic reasons. However, these cannot deliver a sufficient level of positional accuracy on account of the frequently occurring inhomogeneity of the basic magnetic field, non-linearities of the gradients, eddy currents and other disruptive influences. This is due to the distortion effects that are well known in MRT diagnostics. Thus, for example, numerous methods for distortion correction that are based on calculating the deviations of the system from the ideal state and correcting the images accordingly are known with regard to MRT. The applications DE 10 337 241 A1 and DE 10 2006 033 248 A1 are cited as examples of such distortion correction methods.

This situation is further aggravated by the fact that the object under examination (e.g., the actual patient) changes electromagnetic fields (therefore also the HF signals) in the system, and thus, a distortion caused by the object under examination or a patient is an additional disruptive factor to the normal distortion, based, for example, on an inhomogeneity of the magnetic fields.

Such distortions result in a poor positional accuracy that is particularly disruptive in dental medicine, since the images are intended to be used, for example, for planning implants and prostheses. In this situation, even small deviations are extremely critical because the implant or prosthesis does not subsequently fit.

High demands on the basic field homogeneity and gradient linearity and also special measures for homogenizing the fields of the HF signals do, however, make MR systems rather expensive and are barely able to compensate for distortion effects caused by the object under examination or a patient.

SUMMARY AND DESCRIPTION

The present embodiments may obviate one or more of the drawbacks or limitations in the related art. For example, an improved alternative to the previous MR systems and methods for carrying out magnetic resonance measurements in the jaw region is provided.

Such a magnetic resonance system according to the present embodiments for tooth imaging includes a magnetic resonance coil element and an intraoral measuring device that measures the position of a number of measuring points situated in the intraoral region. An "intraoral region" is, for example, a complete jaw together with the set of teeth or any part thereof (e.g., where applicable, also only single teeth, and also where applicable with further intraoral tissue such as gum). The magnetic resonance system includes a magnetic resonance coil element ("MR coil element" in the following) that serves to capture raw data for the reconstruction of MR image data from the intraoral region. In this situation, the MR coil element may, as will be described later, be disposed outside or inside the oral cavity (intraorally).

A measuring device that measures the teeth or specific measuring points in the intraoral region may be used in order to use the measurement data obtained to correct the MR image data (e.g., the images captured by the magnetic resonance element). In this situation, measurement data is the data captured by the measuring device. MR image data is the image data reconstructed from the raw data captured by the magnetic resonance system with the magnetic resonance coil element.

The MR image data acquired using MR systems for tooth imaging exhibits relatively strong distortion. This distortion may, however, be corrected according to the present embodiments by an alignment of the MR image data with the separately measured measurement data. As a result, the MR system according to the present embodiments delivers considerably more positionally accurate MR image data overall.

In a method according to the present embodiments for imaging in the intraoral region or for tooth imaging, a magnetic resonance measurement is carried out using a magnetic resonance system having at least one magnetic resonance coil element and an intraoral measuring device. In this situation, raw data is acquired by the magnetic resonance coil element and magnetic resonance image data is reconstructed on the basis thereof. In addition, the positions of a number of measuring points situated in the intraoral region or on at least one tooth are measured by intraoral measuring device, and the magnetic resonance image data is corrected using the measurement data obtained. This may take place in a correction unit that is part of the magnetic resonance system or is connected downstream of the magnetic resonance system.

According to embodiments of the magnetic resonance system and of the method, the distortion correction may be carried out by comparing the measured measurement data with the corresponding MR image data in a correction facility and determining from this comparison, general transformation instructions for correcting the magnetic resonance image from the measurement data.

The MR coil element for capturing raw data for the reconstruction of MR image data from the intraoral region may be designed as a local coil. With regard to such a configuration as a local coil, depending on the intended application and expense, the MR coil element may be disposed outside the oral cavity (e.g., in the form of a head coil or flexible coil) or inside the oral cavity (e.g., as an intraoral coil element). The general construction of such head coils, flexible coils and intraoral coils is known.

In one embodiment of the magnetic resonance system, the local coil and the intraoral measuring device may be integrated in one physical unit. The advantage of such an integrated implementation lies in the ease of handling and in the capability to fix the position of the two elements relative to one another. Such a fixing would make it easier to align the measurement data with the image data because there would be no positional displacement of the two elements relative to one another to compensate for over the duration of the measurements in addition to the distortion correction. An advantageous embodiment of the integrated implementation provides, for example, that the measuring device is integrated into an intraoral MR coil element. Both the measuring device and the MR coil element are used during the capture of the raw data for the reconstruction of MR image data inside the oral cavity.

In another embodiment, the magnetic resonance system may include a bite piece, into which the measuring device may be integrated. Using the bite piece, the object under examination (e.g., a patient) may be forced to bite the teeth together with a constant pressure during the measurement. By fixing the jaws of the patient relative to the magnetic resonance element motion artifacts in the MR image data, for example, are therefore reduced or avoided. This may further increase the positional accuracy.

It may be advantageous if the measuring device in the magnetic resonance system according to the present embodiments is mounted in a defined position with respect to the magnetic resonance element. "Defined position" may be that, for example, a rigid connection of the two components may be present. Given such defined positioning of the two elements with respect to one another, absolute spatial coordinates may be acquired. "Absolute spatial coordinates" in this context may be that the measurement data is acquired in relation to a reference point of the MR coil element or MR system (e.g., the isocenter of the MRT), and a common coordinate system that is henceforth independent of the measuring device may be used for correction of the MR image data.

Alternatively, this issue may be addressed by the measuring device having a position detection device that determines the position of the measuring device relative to the magnetic resonance coil element or magnetic resonance system. Such a position detection device may, for example, include optical, mechanical (e.g., angle meter) and/or magnetic field sensors (e.g., Hall probes) that are used to acquire measurement data for position determination, and a corresponding evaluation unit. Such position detection devices may not only be used inside the oral cavity to acquire the position of the measuring device relative to the MR coil elements, but may also establish a relationship with structures and elements outside the mouth or outside the region under examination or field of view (FoV). An example is the simultaneous position detection of the measuring device relative to the MR coil element and relative to the temporomandibular joints in order, for example, to still also be able to acquire the current jaw positions in addition to the tooth position or a 3D profile of a dental region.

In the magnetic resonance system according to the present embodiments, the measuring device may include an optical or mechanical measuring unit. An optical measuring unit may, for example, be an optical scanner that performs a scan of individual image points or of an entire 3D panorama. An alternative to a scanner is a camera that captures images of individual measuring points (e.g., teeth or 3D profiles). For example, existing implants may be used as measuring points. This is an option, for example, when the measuring points are configured such that the measuring points may be acquired or identified both in the MR image data and also using the measuring device.

If optical measuring units are used, in addition to natural measuring points in the intraoral region artificial markers such as, for example, stripe or point patterns may also be applied or projected onto the jaw or the teeth by a marking unit (e.g., a miniaturized projector). These artificial markers may be acquired by the measuring device (e.g., a miniaturized camera or a scanner). In this situation, projector and camera may be disposed in the immediate spatial vicinity. From the captured measurement data, which may also be present as image data, the three-dimensional surface may be reconstructed relatively simply using triangulation, a method for the optical measurement of distance using the trigonometric functions. Other systems project individual points onto the teeth, the position of which is acquired by a camera or a scanner. These are then used for correcting the MR image data using an alignment of the positions of the landmarks measured by the measuring device with the corresponding landmarks in the acquired MR image data. In this situation, landmarks are characteristic points or regions in the intraoral region that are acquired both by the measuring device and also by the MR coil element and that have been selected or intended for correcting the distortion. These also include the artificial markers that are applied or projected into the intraoral region.

One advantage of these artificial markers, like colored stripes or points, is the fact that the artificial markers may, amongst other things, be acquired more easily by the measuring device than if only certain natural landmarks of the teeth are used for the correction. The precision of the acquisition of the individual measurement data items and thus also the positional accuracy obtained after distortion correction are increased.

Such artificial markers may also be designed from a material that may be acquired relatively simply in a magnetic resonance image. The correction may be performed simply through an alignment of the measurement data from the measuring points acquired by the measuring device and the MR data for these points acquired by the MR coil element. This enables improved distortion correction of the MR images without additional workflow acts. A workflow act is an additional measurement act to be performed or also a change in the measurement configuration or the location of the object under examination. For example, it is not necessary to remove and introduce a further element into the oral cavity. There is also no renewed distortion resulting from the movements of the object under examination.

Examples of mechanical measuring devices are pressure sensors that may be designed as plate-shaped elements that, for example, use a pressure measurement in the masticatory region of the teeth to recognize and measure the surface structure of the molars. These acquired surface structures may be used as anatomical landmarks in the distortion correction of the MR image data.

During the excitation of protons normal in the MRT, teeth and bony structures may not be optimally represented because these materials contain only a small proportion of water protons. Sequences having ultra-short echo times may therefore be used for MR imaging in the intraoral region (e.g., for tooth imaging). Ultra-short echo times may be echo times below 200 µs. Sequences having echo times between 70 and 140 µs may be employed because good visibility of teeth and bones is already achieved in this range. The demands on the magnetic resonance system (e.g., with respect to the switching times between sending and receiving) are not yet excessively high and may therefore be satisfied with normal MRT electronic components.

In a variant that is an alternative to pure proton imaging, fluorine or phosphor imaging is employed. Other nuclei are excited as protons (e.g., $^{19}F$ (fluorine) or $^{31}P$ (phosphor)), which occur in comparatively high concentrations in teeth and bones. The magnetic resonance system used (e.g., also the magnetic resonance coil element) may be designed such that the magnetic resonance system may send or receive, on the corresponding Larmor frequencies, in a 1.5-tesla magnetic resonance system (e.g., at approximately 60.1 MHz for $^{19}F$ or approximately 25.9 MHz for $^{31}P$). Ultra-short echo times may be used.

In one embodiment of the method, in a first act, positions of teeth or tooth regions (e.g., tips of tooth regions) may be measured using the measuring device as anatomical landmarks. In the correction act, these measuring points may be used for the distortion correction of the magnetic resonance image data using an alignment of the positions of the anatomical landmarks measured by the measuring device with corresponding landmarks in the MR image data.

In another embodiment of the method, during distortion correction, surface structures of at least one tooth may be measured, and the correction of the magnetic resonance image data may take place using an alignment of the positions of the surface structures measured by the measuring device with corresponding 3D profiles in the MR image data.

Measuring a greater number of measuring points or the measurement of three-dimensional structures such as tooth surfaces or 3D profiles of rows of teeth permits a further improvement in positional accuracy in the correction act.

In addition to the number of measuring points, the position and the quality of the measuring points are, however, also decisive factors, and careful selection thereof is thus expedient. In one embodiment, only a few measuring points may be used for measurement purposes. For example, the location of the rear molars or the location of the canine teeth (e.g., the tips of the canine teeth) may be defined as corresponding measuring points. These are suitable landmarks that may be recognized relatively well in the MR images and enable a correction using corresponding alignment.

In another embodiment, a largely complete 3D profile that, for example, includes the entire inside of the teeth of one or both jaws is measured. The alignment with the corresponding MR data set may take place by way of a non-rigid registration.

A greater precision of correction and thus an improved positional accuracy may be achieved through a multiple measurement of individual measuring points (e.g., of individual teeth or points in the jaw) or multiple measurement of three-dimensional structures.

Capture of the measurement data (e.g., the measurement of the teeth or of the jaw by the measuring device may take place before, during or after the MR measurement). Alternatively, a measurement may also take place at a plurality of times before and/or during and/or after the MR measurement. The measurement may be performed in different movement states of the jaws. For example, measuring may occur one time with the mouth open and another time with the mouth closed. The measurement data in the form of absolute spatial coordinates is acquired in relation to a reference point (e.g., the isocenter of the MRT, MR coil element or MR system).

BRIEF DESCRIPTION OF THE DRAWINGS

FIG. 1 shows a schematic illustration of an embodiment of a magnetic resonance system;

FIG. 2 shows a schematic illustration of one embodiment of a head coil having an integrated measuring device of a magnetic resonance system.

DETAILED DESCRIPTION OF THE DRAWINGS

Figure 3:
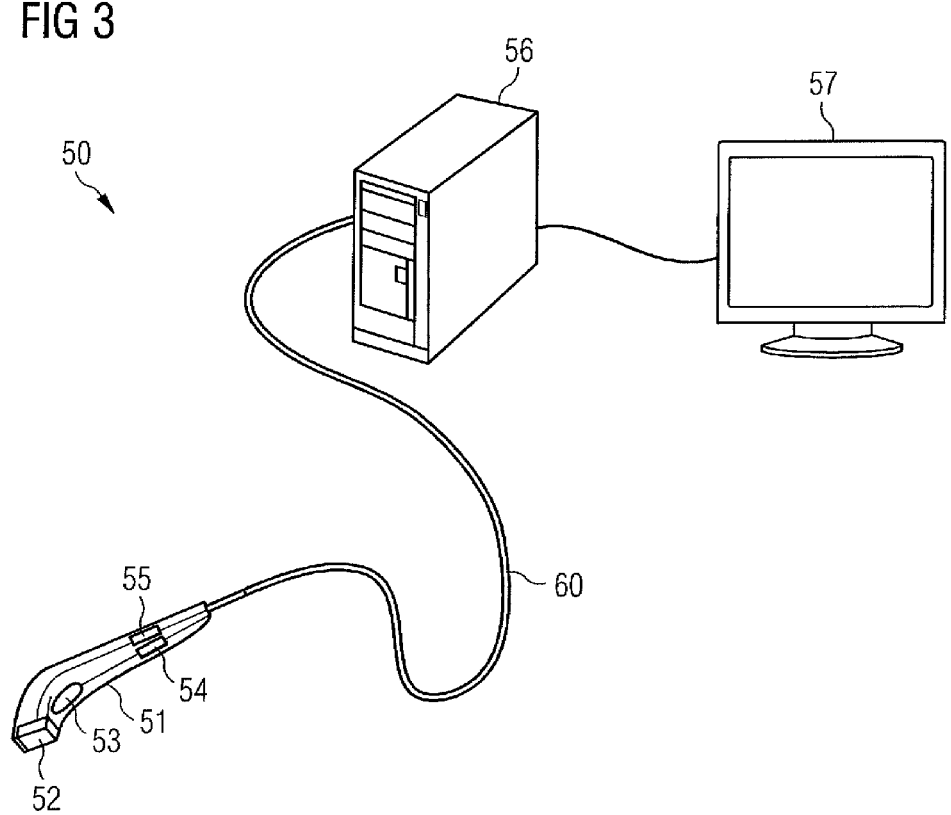
FIG. 3 shows a schematic illustration of one embodiment of a measuring device having an integrated intraoral local coil of a magnetic resonance system.

FIG. 1 shows one embodiment of a magnetic resonance system 1 having at least one magnetic resonance coil element 2 (represented in FIG. 1 only by a body coil) and an intraoral measuring device (not illustrated in the figure) for measuring the intraoral regions of an object under examination 3. The magnetic resonance system 1 also includes a magnetic resonance control and measuring unit 4 that controls magnetic resonance (MR) components (e.g., a basic magnetic field system, a gradient system and a magnetic resonance coil element 2), and in the normal manner, acquires MR raw data and reconstructs images therefrom. This magnetic resonance control and measuring unit 4 includes a plurality of functional units, the construction and mode of operation of which are known and are therefore not described in detail here. The magnetic resonance system 1 includes a measuring device control unit 5 for controlling the intraoral measuring device. The magnetic resonance control and measuring unit 4 and the measuring device control unit 5 are connected upstream of a correction facility 6 (e.g., a correction device). In addition, an image data output device is connected to a processing system including the units 4,5,6.

The intraoral measuring device is introduced in this situation in the oral cavity of the object under examination 3 (not illustrated in FIG. 1 for reasons of clarity). The raw data measured with the magnetic resonance coil element 2 is transferred to the MR coil element control unit 4, which reconstructs the magnetic resonance image data therefrom. At the same or a different time, the position of a plurality of measuring points situated in the jaw (e.g., on at least one tooth) are measured by the intraoral measuring device and transferred to the measuring device control unit 5. The two control units 4,5 transfer the MR image data and the measurement data to the correction facility 6, which compares the obtained measurement data with the MR image data and corrects the MR image data using transformation instructions determined from the comparison. The corrected MR image data may, for example, be output on a suitable image data output device 7 (e.g., a monitor) stored in a memory (not illustrated) or transmitted across a network (not illustrated). The viewer of these MR images corrected in this manner receives distortion-free MR images.

FIG. 2 shows a schematic illustration of one embodiment of an MR coil element 10 in the form of a head coil 10 (e.g., a birdcage coil) having a plurality of antenna rods 15 running parallel and having an integrated measuring device 20 of a magnetic resonance system according to the present embodiments. The head of a patient 100 or subject may be positioned in the head coil 10. The head coil 10 is used to acquire the raw data for the MR image data from outside the oral cavity of the object under examination 100. Integrated in the head coil 10 is the intraoral measuring device 20 that may be introduced from the front into the mouth opening of the patient 100. The intraoral measuring device 20 is provided with a bite piece, on which the patient 100 is intended to bite during the examination.

In alternative embodiments, additional intraoral MR coil elements may be disposed in the intraoral measuring device 20.

FIG. 3 shows a schematic illustration of an embodiment of a combined measurement data and MR data acquisition device 50 in the form of an intraoral hand scanner 51 that includes an intraoral measuring device 52 and an intraoral MR coil element 53 in an integrated construction. Also provided in the hand scanner 51 are an MR coil element control unit 54 and a measuring device control unit 55 that are connected by cable link 60 by way of control unit 56 (including an image data reconstruction unit and a correction unit connected downstream) to an image data output device 57. The MR coil element control unit 54 and the measuring device control unit 55 also serve to preprocess the measured data.

As a result of the integrated construction of the hand scanner 51, the measuring device 52 and the MR coil element 53 may be introduced into the oral cavity in a fixed orientation with respect to one another in order to measure the intraoral region using the measuring device 51 and to simultaneously acquire the MR image data using the MR coil element. This provides that a high positional accuracy of the corrected MR image data may be achieved by a fairly inexpensive system.

In addition to the measuring device 52 and the MR coil element 53, a marking unit may be provided in the hand scanner 51, with which artificial markers may be projected in the intraoral region (e.g., onto the teeth). Alternatively, the measuring device 52 may be designed both as a marking unit and also as a measuring device if, for example, a mini scanner that is equipped with both functionalities is used (e.g., a projection capability and a scanner capability).

The magnetic resonance system and the method described in the foregoing are only exemplary embodiments that may be modified in many different ways by the person skilled in the art without departing from the ambit of the invention. Use of the indefinite article "a" or "an" does not mean that the features in question cannot also be present several times. Moreover, "units" may consist of one or more components that may also be disposed spatially distributed.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance system for carrying out magnetic resonance measurements in an intraoral region, the magnetic resonance system comprising:
    a magnetic resonance coil element operable to acquire raw data for reconstruction of magnetic resonance image data based on the raw data;
    an intraoral measuring device configured to measure a position of a number of measuring points situated in the intraoral region; and
    a correction device configured to correct the magnetic resonance image data using the measured position of the number of measuring points.

2. The magnetic resonance system as claimed in claim 1, wherein the magnetic resonance coil element comprises a local coil.

3. The magnetic resonance system as claimed in claim 2, wherein the local coil and the intraoral measuring device are integrated in one physical unit.

4. The magnetic resonance system as claimed in claim 1, further comprising a bite piece, the intraoral measuring device being integrated in the bite piece.

5. The magnetic resonance system as claimed in claim 1, wherein the intraoral measuring device is mounted in a defined position with respect to the magnetic resonance coil element.

6. The magnetic resonance system as claimed in claim 1, wherein the intraoral measuring device comprises a position detection device operable to determine a position of the magnetic resonance coil element, the magnetic resonance system, or a combination thereof, relative to a reference point.

7. The magnetic resonance system as claimed in claim 1, wherein the intraoral measuring device comprises an optical measuring unit, a mechanical measuring unit, or optical and mechanical measuring units.

8. The magnetic resonance system as claimed in claim 1, further comprising a marking unit for applying, projecting, or applying and projecting artificial markers on teeth, the jaw, or the teeth and the jaw, the artificial markers being acquirable by the intraoral measuring device.

9. The magnetic resonance system as claimed in claim 2, wherein the local coil comprises a head coil or an intraoral coil element.

10. The magnetic resonance system as claimed in claim 8, wherein the artificial markers are acquirable in magnetic resonance image data.

11. A method for carrying out magnetic resonance measurements in an intraoral region using a magnetic resonance system having at least one magnetic resonance coil element and an intraoral measuring device, the method comprising:
   acquiring raw data using the magnetic resonance coil element;
   reconstructing magnetic resonance image data on the basis of the acquired raw data;
   measuring positions of a number of measuring points situated in an intraoral region using the intraoral measuring device; and
   correcting the magnetic resonance image data using the measured positions.

12. The method as claimed in claim 11, wherein high-frequency send sequences having ultra-short echo times are used for acquisition of the raw data.

13. The method as claimed in claim 11, further comprising determining transformation instructions for correcting the magnetic resonance image data from the measured positions.

14. The method as claimed in claim 11, wherein measurement data is captured using optical measuring units, mechanical measuring units, or optical and mechanical measuring units for measuring the positions of the measuring points.

15. The method as claimed in claim 11, wherein positions of teeth or tooth regions are measurable by the intraoral measuring device as anatomical landmarks, and
   wherein the correction of the magnetic resonance image data takes place using an alignment of positions of the anatomical landmarks measured by the intraoral measuring device with corresponding landmarks in the magnetic resonance image data.

16. The method as claimed in claim 15, wherein measuring the positions comprises measuring tips of teeth.

17. The method as claimed in claim 11, wherein surface structures of at least one tooth are measured by the intraoral measuring device, and
   wherein the correction of the magnetic resonance image data takes place using an alignment of positions of the surface structures measured by the intraoral measuring device with corresponding 3D profiles in the magnetic resonance image data.

18. The method as claimed in claim 11, further comprising acquiring absolute spatial coordinates in relation to a reference point of the at least one magnetic resonance coil element, the magnetic resonance system, or a combination thereof.

19. The method as claimed in claim 12, further comprising determining transformation instructions for correcting the magnetic resonance image data from the measured positions.

20. The method as claimed in claim 12, wherein positions of teeth or tooth regions are measurable by the intraoral measuring device as anatomical landmarks, and
   wherein the correction of the magnetic resonance image data takes place using an alignment of positions of the anatomical landmarks measured by the intraoral measuring device with corresponding landmarks in the magnetic resonance image data.

* * * * *